(12) United States Patent
Berger et al.

(10) Patent No.: US 7,223,420 B2
(45) Date of Patent: May 29, 2007

(54) POWDER MIXTURE FOR RESORBABLE CALCIUM PHOSPHATE BIOCEMENTS

(75) Inventors: Georg Berger, Zepernick (DE); Heidi Marx, Berlin (DE); Christian Jäger, Berlin (DE); Jutta Pauli, Berlin (DE)

(73) Assignee: BAM Bundesanstalt für Materialforschung und -prüfung (DE)

( * ) Notice: Subject to any disclaimer, the term of this patent is extended or adjusted under 35 U.S.C. 154(b) by 219 days.

(21) Appl. No.: 10/689,221

(22) Filed: Oct. 20, 2003

(65) Prior Publication Data

US 2004/0086545 A1    May 6, 2004

(30) Foreign Application Priority Data

Oct. 21, 2002  (DE) ............................... 102 49 625

(51) Int. Cl.
| A61L 24/00 | (2006.01) |
| A61K 9/14 | (2006.01) |
| A61K 33/42 | (2006.01) |
| A61K 33/08 | (2006.01) |
| A61K 33/00 | (2006.01) |
| A01N 59/26 | (2006.01) |
| A01N 59/06 | (2006.01) |
| A01N 59/00 | (2006.01) |

(52) U.S. Cl. ................. 424/489; 424/422; 424/423; 424/426; 424/484; 424/602; 424/688; 424/692; 424/724

(58) Field of Classification Search ............. 424/422, 424/423, 426, 484, 489, 602, 688, 692, 724
See application file for complete search history.

(56) References Cited

U.S. PATENT DOCUMENTS

| 3,922,155 | A | * | 11/1975 | Broemer et al. ............ 65/33.3 |
| 4,239,113 | A | * | 12/1980 | Gross et al. ............... 206/568 |
| 5,092,888 | A | | 3/1992 | Iwamoto et al. |
| 6,002,065 | A | * | 12/1999 | Constantz et al. .......... 423/308 |
| 6,117,456 | A | | 9/2000 | Lee et al. |
| 6,495,156 | B2 | | 12/2002 | Wenz et al. |

FOREIGN PATENT DOCUMENTS

| DE | 40 16 135 A1 | 11/1990 |
| DE | 19744809 C1 * | 7/1999 |
| EP | 0 237 043 B1 | 6/1992 |
| EP | 0 541 546 B1 | 10/1994 |
| EP | 1 153 621 A1 | 11/2001 |
| WO | 91/07357 | 5/1991 |
| WO | 99/49906 | 10/1999 |

OTHER PUBLICATIONS

Derwent-Acc-No. 1999-348171 Abstracting DE 19744809C1 Jul. 1, 1999.*

* cited by examiner

*Primary Examiner*—Johann Richter
*Assistant Examiner*—Ernst Arnold
(74) *Attorney, Agent, or Firm*—Akerman Senterfitt (57) ABSTRACT

The present invention relates to a powder mixture for resorbable calcium phosphate biocements, which mixture consists of 40–99% by volume of powder having a particle size of 0.1–10 μm, 1–20% by volume of powder having a particle size of 10–43 μm and 0–59% by volume of powder having a particle size of 43–315 μm, which powder is obtained by grinding the spontaneously crystallizing melts of a material comprising crystalline and X-ray amorphous phases, which material a) according to $^{31}$P-NMR measurements, contains $Q_0$-groups of orthophosphate and $Q_1$-groups of diphosphate, the orthophosphates or $Q_0$-groups making up 65 to 99.9% by weight relative to the total phosphorus content of the powder mixture and the diphosphates or $Q_1$-groups making up 0.1 to 35% by weight relative to the total phosphorus content of the powder mixture, and b) according to X-ray diffractometric measurements and relative to the total weight of the powder mixture, contains 35 to 99.9% by weight of a main crystal phase consisting of various Ca-orthophosphates and 0.1 to 20% by weight of a secondary crystal phase consisting of various Ca-diphosphates and chain phosphates, and c) besides the main crystal phase, contains an X-ray amorphous phase which in total makes up 0.1 to 65% by weight relative to the total weight of the powder mixture.

21 Claims, 4 Drawing Sheets

Fig. 1: The composition according to code 40-30-30 in its initial state (1) and after being stored in SBF for 4 weeks (2)

Fig. 2: The composition according to code 50-25-25 in its initial state (1) and after being stored in SBF for 4 weeks (2)

Fig. 3: The composition according to code GA 1 in its initial state (1) and after being stored in SBF for 4 weeks (2)

Fig. 4a: Comparison of the spectra of the 40-30-30 sample before and after being stored in SBF Fig. 4b: Comparison of the spectra of the 40-30-30 sample before and after being stored in SBF

POWDER MIXTURE FOR RESORBABLE CALCIUM PHOSPHATE BIOCEMENTS

BACKGROUND OF THE INVENTION

1. Field of the Invention

The present invention relates to powder mixtures based on calcium phosphates. The invention also relates to the use of the aforesaid powder mixtures for manufacturing biocements with high solubility which only contain the crystal phases currently known after setting, i.e. hydroxyapatite (HA), precipitated apatite (PHA) and calcium-deficient hydroxyapatite (Ca-d-HA), in subordinate amounts, i.e. as secondary phases.

2. Description of the Related Art

In principle, inorganic materials which are easily resorbed are known. Materials which are specifically used as bioactive bone replacement materials and dissolve quickly have also been described in the relevant literature. For example, there have been numerous publications dedicated to the successful clinical use of ceramic materials the main crystal phases of which are alpha- or beta-tricalcium phosphate (TCP). In addition, there have been comparative analyses of these two TCP phases using animal tests. With regard to the following explanations, special attention must be drawn to an alpha-TCP containing dicalcium phosphate on the surface of granulated materials made thereof, whose solubility was higher than that of the pure alpha-PCT core material, especially in the initial phase following an implantation (EP 0237043 B1).

The chemical solubility of the aforesaid granulated materials was surpassed by other bioactive materials based on calcium phosphates which in addition contain oxides of potassium, sodium, magnesium and/or silicon (EP 541564 B1) and the glassy-crystalline material of which is based on the following main crystal phases: Phase X, rhenanite, phase according to Ando (Phase A) and/or mixed crystals derived from the aforesaid phases.

The aforesaid products are obtained by melting processes, they contain orthophosphates and a glass phase and their individual phase constituents are distributed in a homogenous manner, but they are not known to have been processed into cements.

Instead, inorganic biocements have been composed using powder mixtures made up of various calcium phosphates, as disclosed e.g. in EP 1153621 or U.S. Pat. No. 5,129,905.

SUMMARY OF THE INVENTION

The object of the invention is to provide a powder which is based on a product obtained by a melting process and which can set directly after mixing with water or an aqueous solution and which preferably comprises alkaline earth-alkali orthophosphates once it has set whose solubility is higher than that of apatitic phase constituents, especially when making up the major part of a phase.

According to the invention, the powder mixture for resorbable calcium phosphate biocements is characterized by a fraction mixture consisting of (relative to the total volume of the powder mixture):

40–99% by volume of powder having a particle size of 0.1–10 μm

1–20% by volume of powder having a particle size of 10–43 μm

0–59% by volume of powder having a particle size of 43–315 μm which powder is obtained by grinding the spontaneously crystallizing melts of a material comprising crystalline and X-ray amorphous phases, which material a) according to $^{31}$P-NMR measurements, contains $Q_0$-groups of orthophosphate and $Q_1$-groups of diphosphate, the orthophosphates or $Q_0$-groups making up 65 to 99.9% by weight relative to the total phosphorus content of the powder mixture and the diphosphates or $Q_1$-groups making up 0.1 to 35% by weight relative to the total phosphorus content of the powder mixture, and b) according to X-ray diffractometric measurements and relative to the total weight of the powder mixture, contains 35 to 99.9% by weight of a main crystal phase selected from the group consisting of $Ca_2K_{1-x}Na_{1+x}(PO_4)_2$, where x=0.1 to 0.9, $Ca_{10}Na(PO_4)_7$, $Ca_{10}K(PO_4)_7$, mixtures thereof and mixed crystals according to the general formula $Ca_{10}K_xNa_{1-x}(PO_4)_7$, where x=0 to 1, and 0.1 to 20% by weight of a substance selected from the group consisting of $Na_2CaP_2O_7$, $K_2CaP_2O_7$, $Ca_2P_2O_7$, $NaPO_3$, $KPO_3$ and mixtures thereof as a secondary crystal phase, and c) besides the main crystal phase, contains an X-ray amorphous phase which in total makes up 0.1 to 65% by weight relative to the total weight of the powder mixture.

Preferably, the mixture contains 0.1–15% by weight, preferably 0.5–4% by weight, chain phosphates selected from among $NaPO_3$, $KPO_3$, mixed crystals thereof and mixtures of the foregoing, which are indicated by $Q_2$-groups in $^{31}$P-NMR measurements.

The orthophosphates preferably make up between 40 and 95% by weight, particularly 50 and 90% by weight.

The diphosphates preferably make up between 1 and 22% by weight, particularly 5 and 22% by weight.

The material (powder mixture) which is suitable for preparing a cement as described above is based on CaO, $P_2O_5$, $Na_2O$, $K_2O$, MgO and optionally $SiO_2$ and consists of (in % by weight): 30 to 55 $P_2O_5$, 25 to 50 CaO, 1 to 20 $Na_2O$, 0.5 to 20 $K_2O$, 0.1 to 13 MgO, 0 to 10 $SiO_2$.

A specially preferred embodiment of a main crystal phase comprising $Ca_2K_{1-x}Na_{1+x}(PO_4)_2$, where x=0.1 to 0.9, contains 40 to 52 $P_2O_5$, 28 to 33 CaO, 8.5 to 13 $Na_2O$, 9.5 to 15 $K_2O$, 1.5 to 3 MgO, 0.1 to 4 $SiO_2$.

A specially preferred embodiment of a main crystal phase comprising $Ca_{10}K_xNa_{1-x}(PO_4)_7$, where x=0 to 1, contains 44 to 54 $P_2O_5$, 34 to 48 CaO, 1.5 to 10.5 $Na_2O$, 1 to 11 $K_2O$, 1.5 to 3 MgO, 0.1 to 4 $SiO_2$.

According to a preferred embodiment, the powder mixture additionally contains up to 30% by weight of a calcium phosphate selected from the group consisting of alpha-tricalcium phosphate, beta-tricalcium phosphate and mixtures thereof besides the powder obtained by a melting process.

According to a further preferred embodiment, the powder mixture additionally contains an active agent selected from the group consisting of antibiotics, other pharmaceutical active agents, disinfectants, bacteriostats and mixtures thereof, preferably antibiotics such as tetracyclines, etc.

In mixed crystals which may be contained in the powder mixture according to the invention, the element Ca may be replaced by Mg in an amount ranging up to 20% by weight relative to the weight of the powder mixture.

A particularly preferred embodiment of the invention consists in a two-component kit wherein one component is the powder mixture according to the invention and the other component is made up of a water phase.

It is therefore preferred that the powder mixture according to the invention be processed into an aqueous solution, a suspension or a paste.

In general, the term "X-ray amorphous material" used herein cannot be clearly defined. "X-ray amorphous" refers to a material whose structure cannot be determined using standard XRD (X-ray diffractometry). The undetectable areas can be very small organized areas (micro-crystalline) as well as statistically unorganized areas. Unlike XRD, the $^{31}$P-NMR results can be used to detect the existence of any crystalline phase. Therefore quantitative estimates based on NMR and XRD results can be rather different. In the present case, this phenomenon seems to be particularly true of the diphosphate and chain phosphate contents; as a rule, $^{31}$P-NMR measurements yield considerably higher contents than XRD and in some cases no contents at all are found using XRD. This impressively shows why $^{31}$P-NMR measurements are an essential prerequisite for characterizing and finally manufacturing the materials according to the invention.

Both crystalline and X-ray amorphous phases can therefore be provided in a thoroughly mixed state. It is of no importance for the present invention whether one phase is located adjacent to the other or one phase encloses the other. The term "main crystal phase" as used herein refers to a crystalline phase which is detected using X-ray diffraction and is contained in an amount exceeding that of a secondary phase by at least one third while concentrations of 20% and below, preferably below 15% by weight, are referred to as secondary crystal phases and should not be surpassed.

For the sake of clarity, it must be pointed out that "$Ca_2KNa(PO_4)_2$" can certainly be identified as main crystal phase, among others. However, there are shifts of intensity in the individual compositions, which may be rather substantial in some cases, due to the varying ratio of sodium to potassium or the inclusion of other ions (e.g. $Mg^{2+}$ or $SiO_4^{4-}$) so that the formula "$Ca_2K_{1-x}Na_{1+x}(PO_4)_2$, where x=0.1–0.9" is to be used.

Higher Na contents are preferred, e.g. x=0.2–0.9.

Surprisingly, it has been found that powders whose composition varies within the range indicated in the invention and which are mixed with pure water or aqueous solutions can set within 2 to 10 min without further additives having necessarily to be used. This effect can probably be put down to the powders having hydraulic and/or latently hydraulic properties. The aforesaid effect increases if diphosphates in the form of the crystalline diphosphates $Na_2CaP_2O_7$, $K_2CaP_2O_7$, $Ca_2P_2O_7$ and/or X-ray amorphous substances are contained in the product obtained by the melting process besides the main crystal phases mentioned hereinbefore, i.e. preferably $Ca_{10}Na(PO_4)_7$, $Ca_{10}K(PO_4)_7$ and/or mixed crystal phases in between said compounds, and X-ray amorphous orthophosphates.

Further, it was surprisingly found that the aforesaid statement can be clearly quantified using $^{31}$P-NMR measurements.

The $^{31}$P-NMR measurements, which were carried out using a superconductive Fourier NMR spectrometer known as Avance DMX400 WB and manufactured by Bruker BioSpin GmbH (Germany), showed that the material consists of 65 to 99.9% orthophosphate of calcium and in some cases orthophosphate of sodium, potassium and magnesium, wherein the aforesaid orthophosphate content is determined using $^{31}$P-NMR measurements ($Q_0$-groups) and refers to crystalline and/or X-ray amorphous material in its entirety, 0.1 to 35% diphosphate of calcium and in some cases diphosphate of sodium, potassium and magnesium, wherein the aforesaid diphosphate content is determined using $^{31}$P-NMR measurements ($Q_1$-groups) and refers to crystalline and/or amorphous material in its entirety, and 0 to 10% chain phosphate consisting of sodium phosphate and/or potassium phosphate, wherein the aforesaid chain phosphate content is determined using $^{31}$P-NMR measurements ($Q_2$-groups) and refers particularly to X-ray amorphous and, as the case may be, crystalline material in its entirety. In addition, 0 to 10% of a silicate phase may be contained, depending upon the amount of $SiO_2$ added.

The diphosphate contents result from a comparatively high phosphate content relative to the other constituents. The aforesaid phosphate content could also be the reason why the compositions according to the invention melt very easily yielding a rather fluid melt compared to known resorbable materials.

Although it is considered advantageous that the setting process can take place using pure water, cations, particularly sodium and potassium, and anions, particularly chlorides, can be added.

The invention also relates to the use of the powder mixture with the composition described hereinbefore for manufacturing resorbable calcium phosphate biocements which contain less than 20% by weight hydroxyapatite (HA) and/or precipitated hydroxyapatite besides their initial main crystal phases once the setting process is finished. This is particularly advantageous as the solubility of HA is lower than that of the main phase according to the invention. HA preferably makes up less than 10% by weight.

In general, a powder mixture having the composition indicated hereinbefore is mixed with pure water or aqueous solutions before use.

Advantageously, the setting process can take place using aqueous solutions containing cations, particularly sodium and potassium, and anions, particularly chlorides.

The aqueous solution may additionally contain cohesion promoters, which may be selected from the groups of hydroxyethyl starch, soluble starch, cyclodextrins, alginates, dextran sulphates, polyvinylpyrrolidone and/or hyaluronic acid, and/or setting accelerators. Preferred cohesion promoters are starch, cyclodextrins and PVP.

Preferably, disodium hydrogen phosphate is added to the aqueous solution as a setting accelerator.

The aqueous solution is mixed with the cement powder at a ratio ranging between 0.15 and 0.4 ml/g, preferably 0.18 and 0.23 ml/g. For example, 0.5 ml water and 2.5 g powder are used to achieve a ratio of 0.2 ml/g.

The material needed to prepare the powder is manufactured by combining the substances suitable for preparing the mixture to be melted, i.e. 30–55% by weight CaO, 35–50% by weight $P_2O_5$, 1–20% by weight $Na_2O$, 0.5–20% by weight $K_2O$ and 0.1–5% by weight MgO and optionally up to 5% by weight $SiO_2$, homogenizing and drying the mixture and subjecting it to a step-by-step thermal treatment lasting 1–2 h at 350–450° C., 750–850° C. and 950–1,050° C. respectively, melting the mixture at between 1,550 and 1,650° C., holding it at the melting temperature for between 10 and 60 minutes and finally cooling the mixture in a spontaneous or temperature-controlled manner and grinding it.

The melting process is carried out in a suitable crucible material, e.g. consisting of a Pt/Rh alloy. The melt is poured, preferably following a holding time of between 10 and 60 min, and once the mass has solidified it is cooled down to room temperature in air (spontaneous cooling) or in a cooling furnace (e.g. at a rate of 1 to 20 degrees/min), depending upon its intended use. The melt can also be blown thus directly forming the melt into spherical granules. In both cases, a spontaneous crystallization process takes place while the melt cools down. The mixture to be melted may comprise oxides, carbonates, hydrogen phosphates and/or orthophosphoric acid. The $^{31}$P-NMR measurements yield different spectra allowing conclusions as to the raw materials used or indicating small amounts of iron oxides or manganese oxides contained therein.

Once the material has cooled down, it is ground, separated into grain size fractions and mixed so that particles ranging between 0.1 and 10 μm make up 40–99% by volume particles ranging between 10 and 43 μm make up 1–20% by volume particles ranging between 43 and 315 μm make up 0–59% by volume if the product obtained by the grinding process does not correspond to the desired spectrum.

Further calcium phosphates may be added, e.g. alpha-tricalcium phosphate, beta-tricalcium phosphate or even $Ca_5Na_2(PO_4)_4$, $CaNaPO_4$ and mixtures thereof, although the three latter are not preferred. The aforesaid substances are added in an amount ranging up to 30% by weight using grain size fractions similar to those of the ground material although this step may reduce the advantage of a thorough mixing of the phases achieved by melting them.

Instead, the advantage consists in that the product obtained by the melting process is ground or a powder mixture is prepared of this single component, if necessary, and in that this single component is mixed with water or an aqueous solution which optionally contains cohesion promoters and/or setting accelerators. The setting process lasts between 2 and 10 min. The sample bodies produced in vitro are immediately stored in SBF (simulated body fluid) according to KOKUBO et al. [J.Biomed.Mater.Res. 24 (1990)721–734], in which solution they remain mechanically stable and do not disintegrate during a period of 4 weeks.

The aforesaid stability is in no way affected by a pharmaceutical active agent, an antibiotic, a disinfectant or bacteriostat which may be added to the powder or powder mixture before combining it with water or an aqueous solution.

The invention will hereinafter be explained in detail by means of examples. All percentages are by weight unless indicated otherwise.

EXAMPLE 1

The following materials were synthesized according to the amounts indicated in the table in % by weight:

| Code | CaO | MgO | $P_2O_5$ | $Na_2O$ | $K_2O$ | $SiO_2$ |
|---|---|---|---|---|---|---|
| GA 1 | 30.67 | 2.45 | 43.14 | 9.42 | 14.32 | 0.00 |
| GA 2 | 29.92 | 2.39 | 44.53 | 9.19 | 13.97 | 0.00 |
| GA 3 | 29.21 | 2.33 | 45.85 | 8.97 | 13.64 | 0.00 |

To facilitate understanding, this melting process can also be described as follows: GA 1; GA 2(=GA 1+2.5% $P_2O_5$); GA 3(=GA 1+5% $P_2O_5$)

The mixtures to be melted were weighed in as follows:

| Code | $CaCO_3$ in g | MgO in g | 85% $H_3PO_4$ in ml | $Na_2CO_3$ in g | $K_2CO_3$ in g | $SiO_2$ in g |
|---|---|---|---|---|---|---|
| GA 1 | 54.74 | 2.45 | 41.48 | 16.11 | 21.01 | 0 |
| GA 2 | 53.40 | 2.39 | 42.82 | 15.72 | 20.50 | 0 |
| GA 3 | 52.13 | 2.33 | 44.09 | 15.34 | 20.01 | 0 |

First, the components comprising calcium, magnesium, sodium and potassium and optionally silicon are weighed in. Once the weighing-in process is finished, each mixture is mixed in a tumbling mixer for one hour. Then the 85% orthophosphoric acid is added to the mixture, the mixture is thoroughly ground in a mortar, stirred and dried at 100° C. for one hour, ground in a mortar again and stored once more in a drying chamber at 100° C. for one hour. Subsequently, the mixture was once again ground in a mortar, filled into a Pt/Rh crucible and heated up to 400° C., at which temperature it was held for one hour, then heated up to 800° C., at which temperature it was again held for one hour, and then heated up to 1,000° C., at which temperature it was also held for one hour. The sinter cake produced in this way was cooled in air and ground in a mortar again in order to make it more homogeneous. The pretreated mixture was then filled into a platinum crucible and heated up to 1,600° C. in a melting furnace. Once the aforesaid temperature had been reached, the melt was maintained at this temperature for half an hour. The low-viscosity, homogeneous melts were then poured onto a steel plate and pressed using a second steel plate so that a salt-like solidified plate was obtained. The crystallization taking place during this stage gives an opaque, white colour to the bodies obtained by the melting process.

EXAMPLE 2

Following the same production procedure as described in Example 1, i.e. preparing a mixture of calcium carbonate, sodium carbonate, potassium carbonate and orthophosphoric acid, the following compositions were synthesized according to the amounts indicated in the table in % by weight:

| Code | CaO | MgO | $P_2O_5$ | $Na_2O$ | $K_2O$ | $SiO_2$ |
|---|---|---|---|---|---|---|
| GA 4 | 31.54 | 1.19 | 42.37 | 9.17 | 13.95 | 1.78 |
| GA 5 | 30.79 | 1.16 | 43.74 | 8.95 | 13.62 | 1.73 |

Low-viscosity melts were obtained for all compositions, which melts spontaneously crystallized when being cooled. The crystallization products had a white colour.

EXAMPLE 3

Another manufacturing option consists, inter alia, in that the amount of phosphorus or phosphate may be brought in by means of a calcium carrier, either in its entirety or, as in the present example, in part. The following composition was synthesized according to the amounts indicated in the table in % by weight:

| Code | CaO | MgO | $P_2O_5$ | $Na_2O$ | $K_2O$ | $SiO_2$ |
|---|---|---|---|---|---|---|
| GA 1 | 30.67 | 2.45 | 43.14 | 9.42 | 14.32 | 0.00 |

The mixture to be melted was weighed in as follows:

| Code | $CaCO_3$ in g | Magnesium hydroxide carbonate in g | 85% $H_3PO_4$ in ml | $Na_2CO_3$ in g | $K_2CO_3$ in g | $CaHPO_4$ in g |
|---|---|---|---|---|---|---|
| GA 1 | 0.00 | 5.13 | 4.25 | 16.11 | 21.00 | 74.43 |

The mixture to be melted was weighed in according to the amounts indicated above, mixed in a tumbling mixer for one hour, phosphoric acid was added, the mixture was dried at 100° C. for one hour, cooled in air and ground in a mortar. The aforesaid mixture was filled into a platinum crucible, placed in a furnace which had been preheated to 450° C. and held at this temperature for 16 hours. The crucible was taken out and the furnace was preheated to 750° C., which temperature was maintained for 4 hours, and the furnace was then preheated to 950° C., at which temperature the mixture was held for 6 hours. Subsequently, the sample was heated up to 1,600° C. and held at this temperature for half an hour. The low-viscosity, homogeneous melt was then poured onto a steel plate and pressed using a second steel plate so that a salt-like solidified plate was obtained. The crystallization taking place during this stage gives an opaque, white colour to the bodies obtained by the melting process. A discoloration can be observed, depending upon the $CaHPO_4$ component used and undesirable amounts of iron and/or manganese contained therein.

It is also possible to quench the melt in a water bath once the melting process (1,600° C., 0.5 h holding time) is finished (fritting) in order to facilitate the further comminution of the product obtained by the melting process.

EXAMPLE 4

Following the same production procedure as described in Example 1, i.e. preparing a mixture of calcium carbonate, sodium carbonate, potassium carbonate and orthophosphoric acid, the following compositions were synthesized according to the amounts indicated in the table in % by weight:

| Code | CaO | MgO | $P_2O_5$ | $Na_2O$ | $K_2O$ | $SiO_2$ |
|---|---|---|---|---|---|---|
| 50-25-25 | 39.86 | 1.25 | 46.82 | 4.79 | 7.28 | 0 |
| 60-20-20 | 37.99 | 1.49 | 46.08 | 5.73 | 8.71 | 0 |
| 40-30-30 | 41.74 | 1 | 47.58 | 3.84 | 5.84 | 0 |
| 80-10-10 | 34.31 | 1.97 | 44.6 | 7.59 | 11.53 | 0 |
| 60-30-10 | 39.05 | 1.48 | 45.13 | 5.69 | 8.65 | 0 |
| 50-40-10 | 41.43 | 1.23 | 45.39 | 4.74 | 7.21 | 0 |
| 50-32.5-17.5 | 40.65 | 1.24 | 46.1 | 4.77 | 7.24 | 0 |
| 40-50-10 | 43.8 | 0.99 | 45.65 | 3.79 | 5.77 | 0 |
| 40-40-20 | 42.78 | 0.99 | 46.61 | 3.82 | 5.8 | 0 |
| 30-50-20 | 45.16 | 0.75 | 46.88 | 2.86 | 4.35 | 0 |
| 20-50-30 | 46.55 | 0.5 | 48.11 | 1.92 | 2.92 | 0 |
| 30-0-70 | 40.1 | 0.73 | 52.04 | 2.83 | 4.3 | 0 |
| 50-0-50 | 37.4 | 1.23 | 49.5 | 4.71 | 7.16 | 0 |
| 70-0-30 | 34.71 | 1.72 | 46.96 | 6.59 | 10.02 | 0 |
| 50-40-10-Si | 41.4 | 1.3 | 44.4 | 10.2 | 1.7 | 1 |

Low-viscosity melts were obtained for all compositions, which melts spontaneously crystallized when being cooled. The crystallization products had a white colour.

EXAMPLE 5

$^{31}$P-MAS-NMR spectra of the samples according to Example 1 and Example 2 were recorded with a waiting time of 120 s between the individual pulses. The samples rotated at a speed of 12.5 kHz.

The quantitative composition of the samples as regards their phosphate content is indicated in the following table:

| Code | Orthophosphate content $[(PO_4)^{3-}]$ in % | Diphosphate content $[(P_2O_7)^{2-}]$ in % | Chain phosphate content [predominantly $(PO_3)^{1-}$] in % |
|---|---|---|---|
| GA 1 | 99.5–96 | 0.5–4 | — |
| GA 2 | 88 | 12 | — |
| GA 3 | 79 | 21 | — |
| GA 4 | 95 | 5 | — |
| GA 5 | 89 | 11 | — |

The range indicated for the composition GA 1 is based on the analysis of three batches one of which was synthesized according to the manufacturing method described in Example 3, whereas only one sample was analysed for each of the other compositions.

EXAMPLE 6

$^{31}$P-MAS-NMR spectra of selected samples according to Example 4 were recorded with a waiting time of 120 s between the individual pulses. The samples rotated at a speed of 12.5 kHz.

The quantitative composition of the samples as regards phosphorus is indicated in the following table:

| Code | Orthophosphate content $[(PO_4)^{3-}]$ in % | Diphosphate content $[(P_2O_7)^{2-}]$ in % | Chain phosphate content [predominantly $(PO_3)^{1-}$] in % |
|---|---|---|---|
| 50-40-10 | 92.5 | 7.5 | — |
| 50-32.5-17 | 93 | 7 | — |

-continued

| Code | Orthophosphate content [(PO$_4$)$^{3-}$] in % | Diphosphate content [(P$_2$O$_7$)$^{2-}$] in % | Chain phosphate content [predominantly (PO$_3$)$^{1-}$] in % |
|---|---|---|---|
| 50-25-25 | 86 | 14 | — |
| 40-50-10 | 91 | 9 | — |
| 40-40-20 | 84 | 16 | — |
| 40-30-30 | 82.5 | 13 | 4.5 |
| 30-50-20 | 88 | 9 | 3 |
| 20-50-30 | 73 | 27 | — |
| 60-20-20 | 92 | 8 | — |

EXAMPLE 7

In the zirconium oxide bowl (250 ml) of a planetary mill (200 rpm), 30 g of the product obtained by the melting process having a composition corresponding to code GA 1 according to Example 1 was ground three times for 20 min. The result is shown in the following table.

| Code | D$_{50}$ value [in μm] |
|---|---|
| GA 1 | 8.79 |

EXAMPLE 8

In the zirconium oxide bowl (250 ml) of a planetary mill (200 rpm), 30 g of the products obtained by the melting process having a composition corresponding to codes 30-50-20, 40-30-30, 50-25-25 and 60-20-20 according to Example 4 was ground under the same conditions (three times for 20 min).

| Code | D$_{50}$ value [in μm] |
|---|---|
| 30-50-20 | 4.21 |
| 40-30-30 | 9.08 |
| 50-25-25 | 8.78 |
| 60-20-20 | 8.30 |

EXAMPLE 9

2.5 g powder of the compositions corresponding to code 50-25-25 or 40-30-30 or 60-20-20 produced according to Example 8 was mixed with 0.5 ml water (E-pure water) and filled into 8 mm high moulds having a diameter of 10 mm. The powder/water mixture had set to a sufficient degree after three minutes and could be removed from the mould without any problem. Once a total time of 5 minutes after mixing had passed, the samples were stored in SBF solution (pH=7.4; 37° C. in an incubator at 75 rpm) without signs of disintegration being observed. The samples were stored in SBF either for 1 day or 4 weeks, depending upon the characteristics which were to be examined later.

EXAMPLE 10

2 g powder of the composition corresponding to code GA 1 produced according to Example 7 and 0.2g Ca(H$_2$PO$_4$)$_2$·H$_2$O were mixed with 0.5 ml water (E-pure water) and filled into 8 mm high moulds having a diameter of 10 mm. The powder/water mixture had set to a sufficient degree after three minutes and could be removed from the mould without any problem. Once a total time of 5 minutes after mixing had passed, the samples were stored in SBF solution (pH=7.4; 37° C. in an incubator at 75 rpm) with no signs of disintegration being observed. The samples were stored in SBF either for 1 day or 4 weeks, depending upon the characteristics which were to be examined later.

EXAMPLE 11

Figure 1:
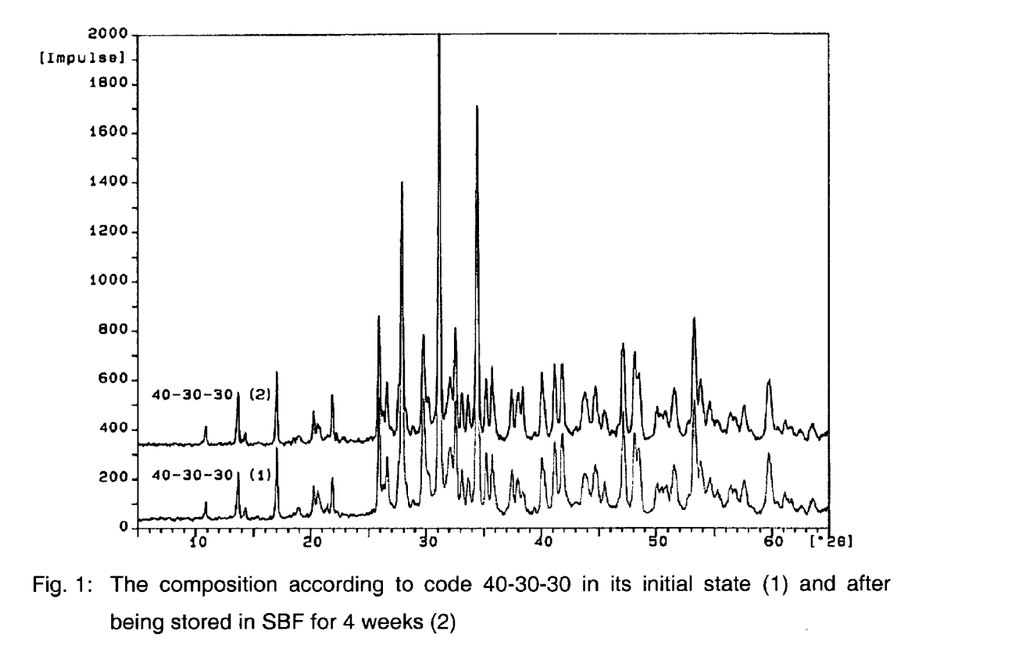
FIG. 1: shows XRD spectra of the material 40-30-30 according to the invention whose composition corresponds to Example 4 and whose phases correspond to Example 6.
Figure 2:
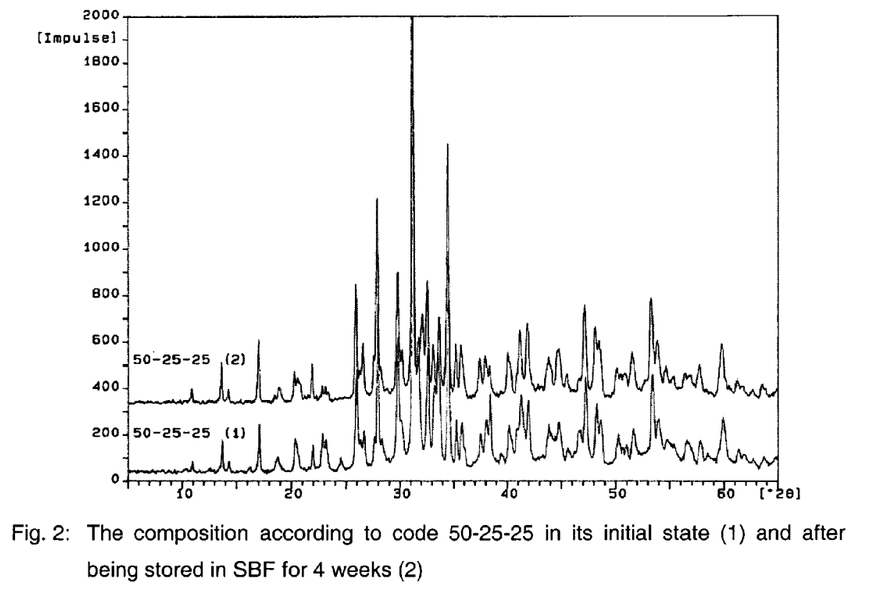
FIG. 2: shows XRD spectra of the material 50-25-25 according to the invention whose composition corresponds to Example 4 and whose phases correspond to Example 6.
Figure 3:
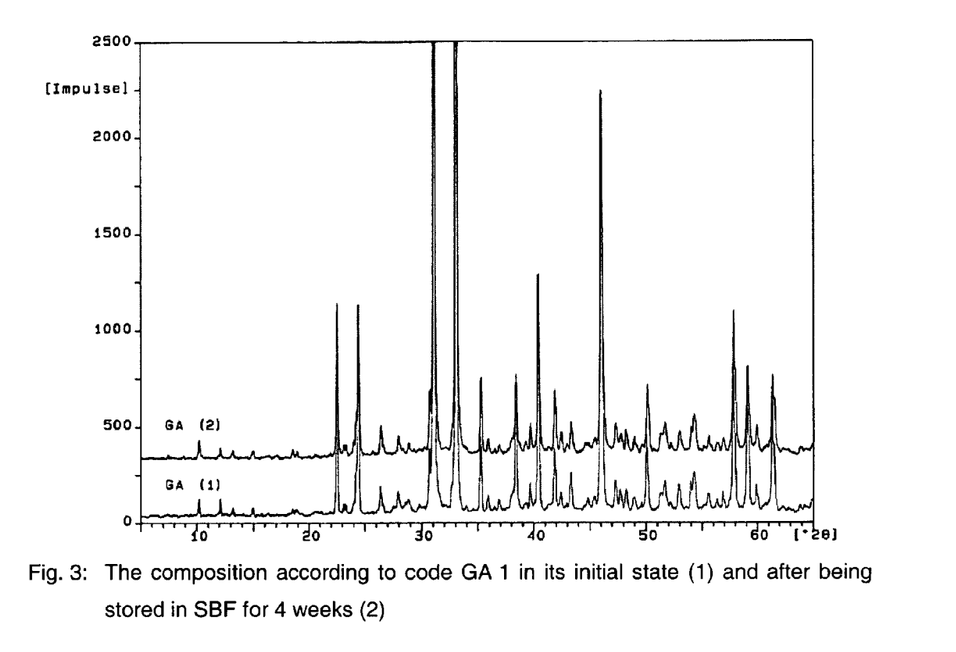
FIG. 3: shows XRD spectra of the composition according to code GA 1 in an initial state (1) and after being stored in SBF for 4 weeks (2)

Samples according to Examples 8 and 9 (compositions corresponding to codes 40-30-30 and 50-25-25; FIG. 1 and FIG. 2) and Examples 7 and 10 (GA 1; FIG. 3) were analysed by means of X-ray diffraction (XRD), the analyses covering the powders in their initial state and samples which had been stored in SBF for 4 weeks and then ground again. The results are shown in FIGS. 1 through 3 according to which there are no significant differences between the individual XRD spectra and the samples do not contain HA, PHA or Ca-d-HA, in particular.

EXAMPLE 12

Figure 4A:
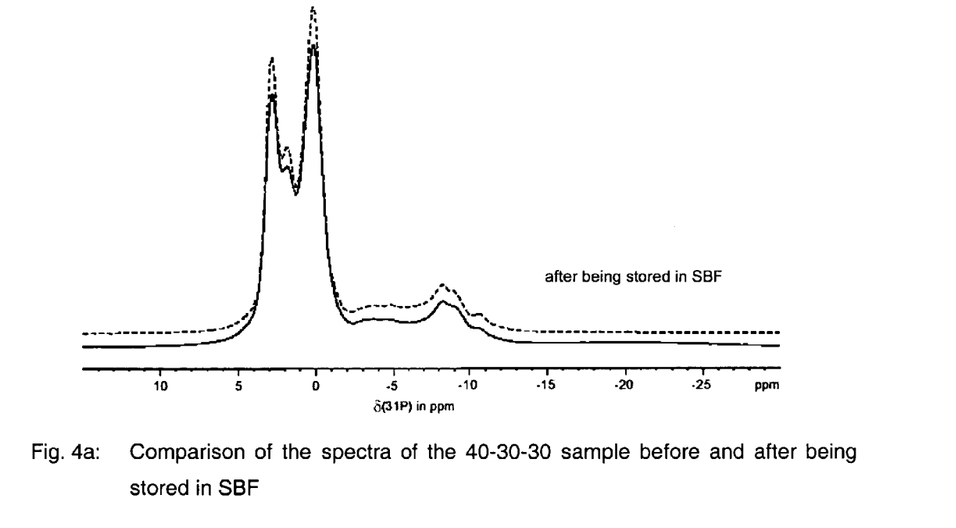
FIG. 4a: shows a comparison of the $^{31}$P-MAS-NMR spectra of the 40-30-30 sample before and after being stored in SBF according to Example 12.
Figure 4B:
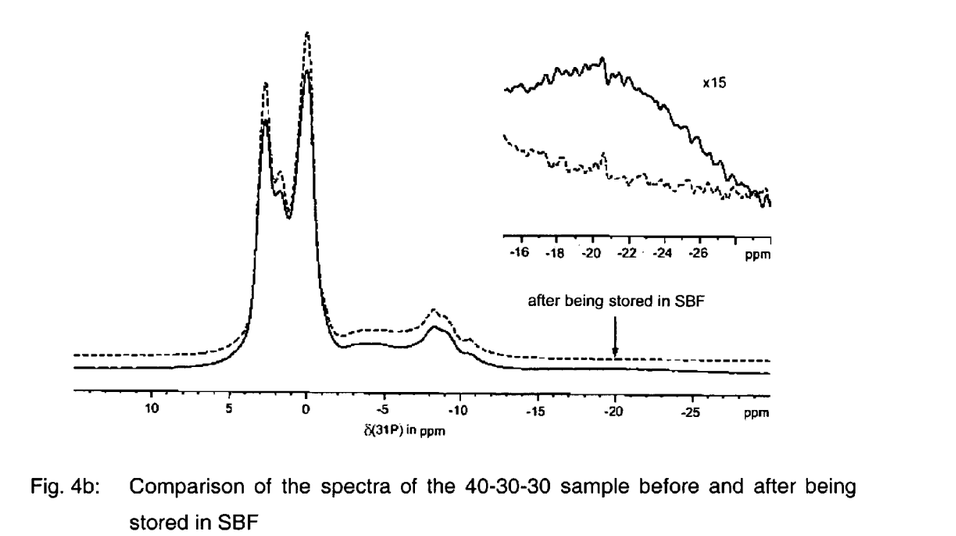
FIG. 4b: shows a comparison of the $^{31}$P-MAS-NMR spectra of the 40-30-30 sample before and after being stored in SBF, including an enlarged view of the −16 ppm to −30 ppm range.

The materials corresponding to codes 50-25-25 and 40-30-30 (FIG. 4a–b) according to Examples 8 and 11 were analyzed using $^{31}$P-MAS-NMR in their initial state and after being stored in SBF for 4 weeks. The result shows that there are no significant differences between the materials in their initial state and the samples stored in SBF for 4 weeks and that only the chain phosphates are no longer present in the 15-fold enlarged view (cf. insert in FIG. 4b).

EXAMPLE 13

Samples of the material corresponding to code 40-30-30 according to Example 11 were stored in SBF for 1 day and their compressive strength was determined to be 3.7 Mpa immediately after taking them out of the solution, i.e. while still being moist, and 6.5 MPa following another 1-day drying process at 110° C.

EXAMPLE 14

Samples of the material corresponding to code 40-30-30 according to Example 11 were stored in SBF for 4 weeks and dried at 110° C. for one day and their compressive strength was determined to be 6.4 MPa. Samples of the material corresponding to code 50-25-25 according to Example 11 were stored in SBF for 4 weeks and dried at 110° C. for one day and their compressive strength was determined to be 6.4 MPa.

The invention claimed is:

1. A powder mixture for resorbable calcium phosphate biocements, characterized by a fraction mixture consisting of, relative to the total volume of the powder mixture:
   40–99% by volume of powder having a particle size of 0.1–10 μm
   1–20% by volume of powder having a particle size of 10–43 μm 0–59% by volume of powder having a particle size of 43–315 μm which powder is obtained by grinding the spontaneously crystallizing melts of a material comprising crystalline and X-ray amorphous phases, which material a) according to $^{31}$P-NMR measurements, contains $Q_0$-groups of orthophosphate and $Q_1$-groups of diphosphate, the orthophosphates or $Q_0$-groups making up 65 to 99.9% by weight relative to the total phosphorus content of the powder mixture and the diphosphates or $Q_1$-groups making up 0.1 to 35% by weight relative to the total phosphorus content of the powder mixture, and b) according to X-ray diffractometric measurements and relative to the total weight of the powder mixture, contains 35 to 99.9% by weight of a main crystal phase selected from the group consisting of $Ca_2K_{1-x}Na_{1+x}(PO_4)_2$, where x=0.1 to 0.9, $Ca_{10}Na(PO_4)_7$, $Ca_{10}K(PO_4)_7$, mixtures thereof and mixed crystals according to the formula $Ca_{10}K_xNa_{1-x}(PO_4)_7$, where x=0 to 1, and 0.1 to 20% by weight of a substance selected from the group consisting of $Na_2CaP_2O_7$, $K_2CaP_2O_7$, $Ca_2P_2O_7$, $NaPO_3$, $KPO_3$ and mixtures thereof as a secondary crystal phase, and c) besides the main crystal phase, contains an X-ray amorphous phase which in total makes up 0.1 to 65% by weight relative to the total weight of the powder mixture and which material is prepared by combining the substances 30–55% by weight CaO, 35–50% by weight $P_2O_5$, 1–20% by weight $Na_2O$, 0.5–20% by weight $K_2O$ and 0.1–5% by weight MgO and optionally up to 5% by weight $SiO_2$, homogenizing and drying the mixture and subjecting it to a step-by-step thermal treatment lasting 1–2 h at 350–450° C., 750–850° C. and 950–1,050° C. respectively, melting the mixture at between 1,550 and 1,650° C., holding it at the melting temperature for between 10 and 60 minutes and finally cooling the mixture in a spontaneous or temperature-controlled manner and grinding it.

2. A powder mixture according to claim 1, wherein said mixture contains 0.1–15% by weight, preferably 0.5–4% by weight chain phosphates selected from the group consisting of $NaPO_3$, $KPO_3$, mixed crystals thereof and mixtures of the foregoing, which are indicated by $Q_2$-groups in $^{31}$P-NMR measurements.

3. A powder mixture according to claim 1, wherein the orthophosphates make up 40 to 95% by weight.

4. A powder mixture according to claim 3, wherein the orthophosphates make up 50 to 90% by weight.

5. A powder mixture according to claim 1, wherein the diphosphates make up 1 to 22% by weight, preferably 5 to 22% by weight.

6. A powder mixture according to claim 5, wherein the diphosphates make up 5 to 22% by weight.

7. A powder mixture according to claim 1, wherein in the melted or ground state said mixture consists of (in % by weight):

| | | | |
|---|---|---|---|
| 30 | to | 55 | $P_2O_5$ |
| 25 | to | 50 | CaO |
| 1 | to | 20 | $Na_2O$ |
| 0.5 | to | 20 | $K_2O$ |
| 0.1 | to | 13 | MgO |
| 0.0 | to | 10 | $SiO_2$ |

MgO or $SiO_2$ or a mixture thereof making up at least 1% by weight, and the corresponding crystal phases.

8. A powder mixture according to claim 1, wherein said mixture contains up to 10% of a silicate phase.

9. A powder mixture according to claim 1, wherein said mixture additionally contains up to 30% by weight alpha-tricalcium phosphate, beta-tricalcium phosphate or mixtures thereof besides the powder obtained by a melting process.

10. A powder mixture according to claim 1, wherein said mixture additionally contains an active agent selected from the group consisting of antibiotics, other pharmaceutical active agents, disinfectants, bacteriostats and mixtures thereof.

11. A powder mixture according to claim 1, wherein said mixture is provided in the form of an aqueous solution, a suspension or a paste.

12. A powder mixture according to claim 1, wherein in mixed crystals the element Ca is replaced by Mg in an amount ranging up to 20% by weight relative to the weight of the powder mixture.

13. A powder mixture according to claim 1, wherein said mixture is provided in a two-component kit wherein one component is said powder and the other component is made up of a water phase.

14. A method for manufacturing resorbable calcium phosphate biocements which contain less than 20% by weight hydroxyaparite (HA) and/or precipitated hydroxyapatite besides their initial main crystal phases once the setting process of the cement is finished, said method comprising:

grinding the spontaneously crystallizing melts of a material comprising crystalline and X-ray amorphous phases, which material a) according to $^{31}$P-NMR measurements, contains $Q_0$-groups of orthophosphate and $Q_1$-groups of diphosphate, the orthophosphates or $Q_0$-groups making up 65 to 99.9% by weight relative to the total phosphorus content of the powder mixture and the diphosphates or $Q_1$-groups making up 0.1 to 35% by weight relative to the total phosphorus content of the powder mixture, and b) according to X-ray diffractometric measurements and relative to the total weight of the powder mixture, contains 35 to 99.9% by weight of a main crystal phase selected from the group consisting of $Ca_2K_{1-x}Na_{1+x}(PO_4)_2$, where x=0.1 to 0.9, $Ca_{10}Na(PO_4)_7$, $Ca_{10}(PO_4)_7$, mixtures thereof and mixed crystals according to the formula $Ca_{10}K_xNa_{1-x}(PO_4)_7$, where x=0 to 1, and 0.1 to 20% by weight of a substance selected from the group consisting of $Na_2CaP_2O_7$, $K_2CaP_2O_7$, $Ca_2P_2O_7$, $NaPO_3$, $KPO_3$ and mixtures thereof as a secondary crystal phase, and c) besides the main crystal phase, contains an X-ray amorphous phase which in total makes up 0.1 to 65% by weight relative to the total weight of the powder mixture to thereby form a cement powder with a fraction mixture consisting of (relative to the total volume of the powder mixture):

40–99% by volume of powder having a particle size of 0.1–10 μm

1–20% by volume of powder having a particle size of 10–43 μm

0–59% by volume of powder having a particle size of 43–315 μm and which material is prepared by combining the substances 30–55% by weight CaO, 35–50% by weight $P_2O_5$, 1–20% by weight $Na_2O$, 0.5–20% by weight $K_2O$ and 0.1–5% by weight MgO and optionally up to 5% by weight $SiO_2$, homogenizing and drying the mixture and subjecting it to a step-by-step thermal treatment lasting 1–2 h at 350–450° C., 750–850° C. and 950–1,050° C. respectively, melting the mixture at between 1,550 and 1,650° C., holding it at the melting temperature for between 10 and 60 minutes and finally cooling the mixture in a spontaneous or temperature-controlled manner and grinding it.

15. The method according to claim 14, comprising mixing the cement powder with pure water or aqueous solutions.

16. The method according to claim 15, wherein the setting process takes place using aqueous solutions additionally containing canons, particularly sodium and potassium, and anions, particularly chlorides.

17. The method according to claim 16, wherein cohesion promoters and/or setting accelerators are added to the aqueous solution.

18. The method according to claim 17, wherein an least one compound selected from the group consisting of hydroxyethyl starch, soluble starch, cyclodextrins, alginates, dextran sulphates, polyvinylpyrrolidone and/or hyaluronic acid are selected as cohesion promoters and disodium hydrogen phosphate is added to the aqueous solution as a setting accelerator.

19. The method according to claim 16, wherein the aqueous solution is mixed with the cement powder at a ratio ranging between 0.15 and 0.4 ml/g, preferably 0.18 and 0.23 ml/g.

20. The method according to claim 14, wherein said resorbable calcium phosphate biocement is provided in the form of an aqueous solution, a suspension or a paste for manufacturing a biodegradable bone replacement material which can be used both for filling defects in vivo and for cultivating cells in vitro in tissue engineering.

21. A biodegradable implant having an open-pore or closed-pore structure, which implant is manufactured using a mixture which is provided in the form of an aqueous solution, a suspension or a paste and has set ex vivo, wherein said mixture is based on a powder mixture for resorbable calcium phosphate biocements, characterized by a fraction mixture consisting of, relative to the total volume of the powder mixture:

40–99% by volume of powder having a particle size of 0.1–10 μm

1–20% by volume of powder having a particle size of 10–43 μm

0–59% by volume of powder having a particle size of 43–315 μm which powder is obtained by grinding the spontaneously crystallizing melts of a material comprising crystalline and X-ray amorphous phases, which material a) according to $^{31}$P-NMR measurements, contains $Q_0$-groups of orthophosphate and $Q_1$-groups of diphosphate, the orthophosphates or $Q_0$-groups making up 65 to 99.9% by weight relative to the total phosphorus content of the powder mixture and the diphosphates or $Q_1$-groups making up 0.1 to 35% by weight relative to the total phosphorus content of the powder mixture, and b) according to X-ray diffractometric measurements and relative to the total weight of the powder mixture, contains 35 to 99.9% by weight of a main crystal phase selected from the group consisting of $Ca_2K_{1-x}Na_{1+x}(PO_4)_2$, where x=0.1 to 0.9, $Ca_{10}Na(PO_4)_7$, $Ca_{10}K(PO_4)_7$, mixtures thereof and mixed crystals according to the formula $Ca_{10}K_xNa_{1-x}(PO_4)_7$, where x=0 to 1, and 0.1 to 20% by weight of a substance selected from the group consisting of $Na_2CaP_2O_7$, $K_2CaP_2O_7$, $Ca_2P_2O_7$, $NaPO_3$, $KPO_3$ and mixtures thereof as a secondary crystal phase, and c) besides the main crystal phase, contains an X-ray amorphous phase which in total makes up 0.1 to 65% by weight relative to the total weight of the powder mixture and which material is prepared by combining the substances 30–55% by weight CaO, 35–50% by weight $P_2O_5$ 1–20% by weight $Na_2O$, 0.5–20% by weight $K_2O$ and 0.1–5% by weight MgO and optionally up to 5% by weight $SiO_2$, homogenizing and drying the mixture and subjecting it to a step-by-step thermal treatment lasting 1–2 h at 350–450° C., 750–850° C. and 950–1,050° C. respectively, melting the mixture at between 1,550 and 1,650° C., holding it at the melting temperature for between 10 and 60 minutes and finally cooling the mixture in a spontaneous or temperature-controlled manner and grinding it.

* * * * *